United States Patent [19]

Garwood et al.

[11] 3,937,791
[45] Feb. 10, 1976

[54] ALUMINA REMOVAL FROM CRYSTALLINE ALUMINO-SILICATES WITH CR(III) SOLUTIONS

[75] Inventors: William E. Garwood, Haddonfield; Nai Yeun Chen, Titusville; Stanley J. Lucki, Runnemede, all of N.J.

[73] Assignee: Mobil Oil Corporation, New York, N.Y.

[22] Filed: Aug. 17, 1973

[21] Appl. No.: 389,109

Related U.S. Application Data

[63] Continuation-in-part of Ser. No. 129,108, March 29, 1971, abandoned.

[52] U.S. Cl............. 423/328; 423/118; 252/455 Z; 208/120
[51] Int. Cl.$^2$..................... C01B 33/28; B01J 29/06
[58] Field of Search......... 252/455, 455 Z; 208/120; 423/328, 329, 330, 118

[56] References Cited
UNITED STATES PATENTS

| | | | |
|---|---|---|---|
| 3,374,182 | 3/1968 | Young................................ | 252/455 |
| 3,459,815 | 8/1969 | Noddings...................... | 423/328 UX |
| 3,652,459 | 3/1972 | Partasarathy.................... | 252/455 Z |
| 3,691,099 | 9/1972 | Young............................. | 252/455 Z |
| 3,794,600 | 2/1974 | Schutt............................ | 252/455 Z |
| 3,803,256 | 4/1974 | Kirsch et al..................... | 208/136 X |
| 3,836,561 | 9/1974 | Young......................... | 252/455 Z X |

OTHER PUBLICATIONS

Pansevich–Kolyada et al., Chemical Abstracts, Vol. 72, June 15, 1970, No. 125391w.
Ermolenko et al., Chemical Abstracts, Vol. 64, 1966, Col. 17093c.

*Primary Examiner*—Oscar R. Vertiz
*Assistant Examiner*—Brian E. Hearn
*Attorney, Agent, or Firm*—Charles A. Huggett; Raymond W. Barclay; Dennis P. Santini

[57] ABSTRACT

A method of removing alumina from a crystalline aluminosilicate composition having a silica/alumina mole ratio of from above 3 to about 12 which comprises heating said aluminosilicate composition to a temperature of greater than 50°C. to about 100°C. in the presence of a cationic form of chromium, preferably $Cr^{+3}$, in aqueous solution of above 0.01 Normal of a chromium salt of a mineral acid whereby the pH is less than 3.5, and such that the atomic ratio of chromium to aluminum is greater than 0.5 for a time sufficient to remove the alumina. The method of this invention permits the aluminosilicate composition to retain substantial crystallinity. Organic compound conversion with the dealuminized material formed by the method of this invention may be advantageously utilized.

14 Claims, No Drawings

ALUMINA REMOVAL FROM CRYSTALLINE ALUMINO-SILICATES WITH CR(III) SOLUTIONS

CROSS-REFERENCE TO RELATED APPLICATION

This is a continuation-in-part of application Ser. No. 129,108, filed Mar. 29, 1971, now abandoned.

BACKGROUND OF THE INVENTION

1. Field of the Invention

This invention relates to the treatment of crystalline aluminosilicate compositions, especially crystalline aluminosilicate zeolites, with an ionic source of chromium whereby alumina is caused to be removed from the aluminosilicate composition. More particularly, this invention is directed to increasing the sorption capacity and the pore diameter of porous crystalline aluminosilicate zeolites having ordered three-dimensional networks of pores and channels by removal of alumina from the zeolite. This invention is further directed to incorporating a form of chromium into the zeolite in a non-ionic form where it can function, under appropriate conditions, as an oxidation catalyst. Thus, the invention is directed to a method of alumina removal, the resultant compositions and hydrocarbon conversion with the resultant compositions, especially cracking and oxidation.

2. Discussion of the Prior Art

Crystalline aluminosilicates have been contacted previously with sources of chromium. Thus, it is known to contact a zeolite with a solution of a chromium salt for purposes of ion exchange. U.S. Pat. No. 3,232,762 discloses room temperature ion exchange of the sodium form of zeolite Y employing an aqueous solution of $CrCl_3.6H_2O$. The final water washed material, pursuant to an example, contained 9.9 weight percent $Cr_2O_3$ (or 6.7 weight percent chromium) and 2.9 weight percent $Na_2O$. These data indicate that the chromium chloride treatment of the zeolite is an ion exchange, chromium for sodium.

The Russian workers N. F. Ermolenko and L. V. Pansevich-Kolyada (Materialy Vses. Soveshch. po Tseolitam, 2nd, Leningrad 1964, pub. 1965, 171–178) reported that a zeolite A was prepared with alumina replaced by $Cr_2O_3$ via an ion exchange of chromium for aluminum. The method of Ermolenko et al. differs greatly from that of the present invention in that zeolite A has a $SiO_2/Al_2O_3$ mole ratio of only 1.85 ± 0.5 (U.S. Pat. No. 2,882,243) and the treatment temperature was 110°C. The present invention requires that the $SiO_2/Al_2O_3$ mole ratio be greater than 3 to about 12 for the very important reason that when said ratio is 3 or less, and an acidic medium is used, i.e., one having a pH of less than 3.5 as in the present invention, the crystal structure is destroyed. The object of the method of the present invention is to maintain the crystallinity under the conditions employed for the subsequent benefits rendered thereby.

The Russians (L. V. Pansevich-Kolyada et al.) again reported (Vesti Akad. Navuk Belarus. SSR. Ser. Khim. Navuk, 1970, (1), 85–89) that they prepared $Cr^{+3}$-containing zeolite A, X, Y and M by ion exchange of the zeolite with 0.01N chromium acetate solution. Only minimal exchange was obtained and, when the concentration of chromium acetate was increased, the crystal structures were destroyed (Note that zeolite X has a $SiO_2/Al_2O_3$ mole ratio of 2.5 ± 0.5, U.S. Pat. No. 2,882,244, and zeolite M has a ratio of 2.1 ± 0.1, U.S. Pat. No. 2,995,423). Although zeolite Y has a $SiO_2/Al_2O_3$ mole ratio of between 3 and 6, their treatment conditions are different from those required in the present invention for effective removal, as opposed to exchange, of alumina (exemplified in Example 18 hereinafter).

In U.S. Pat. No. 3,459,815, there is disclosed a method of ion exchange of montmorillonite clay with a chromium salt. The ratio of chromium to aluminum in the patent method is less than 0.5, whereas said ratio required by the method of the present invention is greater than 0.5.

It is known, therefore, that zeolites generally can be treated with a source of chromium. However, the prior art has not revealed a method whereby a source of chromium can be used to substantially increase the sorption capacity of porous crystalline aluminosilicates by removal of substantial quantities of alumina as in the present invention. Moreover, not only is the alumina removed, but chromium is placed within the composition in a nonionic manner where it is available to function as an oxidation component. Treatment of crystalline aluminosilicates with a chromium salt of a mineral acid has heretofore, in the absence of the critical process parameters herein required, only provided ionically exchanged zeolites with no significant alumina removal while maintaining a substantially crystalline structure.

SUMMARY OF THE INVENTION

Broadly, this invention contemplates a process for removing alumina from a crystalline aluminosilicate composition having a $SiO_2/Al_2O_3$ mole ratio of from above 3 to about 12 which comprises heating said aluminosilicate to a temperature of greater than 50°C. to about 100°C. in the presence of a cationic form of chromium in solution of above 0.01 Normal at pH of less than 3.5 for a time sufficient to remove the alumina. The atomic ratio of chromium to aluminum required in the process of this invention is greater than 0.5.

DESCRIPTION OF PREFERRED EMBODIMENTS

It has now been found that alumina can be removed from a crystalline aluminosilicate composition without substantially destroying its crystallinity by high temperature treatment of the aluminosilicate composition with an ionic source of chromium. Such can be accomplished in several ways, all of which require that the aluminosilicate composition and the source of ionic chromium be at a temperature of greater than 50°C. to about 100°C. Temperatures substantially lower than 50°C. do not provide the desired alumina removal nor do they effectuate the deposition of the chromium in a non-exchangeable position within the composition being treated.

The preferred manner of effectuating alumina removal with concomitant increase in pore diameters of porous crystalline aluminosilicate compositions is to contact the composition with a solution of a chromium salt of a mineral acid. The aluminosilicate composition and salt solution are heated to a temperature of greater than 50°C. to about 100°C. and maintained at that temperature until at least about 5 percent by weight of the alumina is removed. Preferably, to insure that at least about 10 percent of the alumina is removed, the hot chromium salt solution is refluxed with the aluminosilicate composition for at least ½ hour. It will be understood that the temperature and duration of the hot chromium salt solution contact is a time-temperature phenomenon. Thus, if one chooses to contact the crystalline aluminosilicate composition and maintain the temperature at 50°C., a longer time will be required to effectuate the alumina removal than if 100°C. is the temperature. Higher temperatures provided by refluxing enable the alumina to be removed in a shorter period of time.

Further, the crystalline aluminosilicate treated in accordance herewith must have a silica/alumina mole ratio of above 3 to about 12 and the atomic ratio of chromium (in the solution of above 0.01 Normal having a pH of less than 3.5) to aluminum in the aluminosilicate must be greater than 0.5.

Crystalline aluminosilicate compositions which can be treated pursuant to the present invention include the crystalline aluminosilicate zeolites. While alumina can readily be removed from a silica/alumina cracking catalyst by the present method, the invention particularly contemplates the removal of alumina from porous zeolites. It should be understood that all crystalline zeolites can be treated, provided their silica/alumina mole ratio is from above 3 to about 12. These include both the natural types and the synthetic types. Non-limiting examples of natural zeolites which can be treated include faujasite, mordenite, erionite, phillipsite and clinoptilolite. Non-limiting examples of synthetic zeolites which can be treated include, in particular, mordenite, zeolites T, Y, synthetic offretite, ZSM-4, ZSM-5 and zeolite Beta. A particularly interesting aspect of the present invention involves the treatment of "dense" zeolites generally characterized by a pore diameter or aperture opening less than about 6 Angstroms. Erionite, offretite, zeolite T, phillipsite and cliniptilolite are all examples of dense zeolites. Generally speaking, these materials do not sorb substantial quantities of normal hexane or cyclohexane. Hence, their use in the catalytic cracking of gas oils has been severely restricted as gas oils contain molecules incapable of entering untreated or only ion exchanged dense zeolites. It will be understood that each zeolite species behaves differently to some extent from other members of the class, but that the present dealuminization procedure is applicable to all such materials.

In employing a chromium salt of a mineral acid to supply ionic forms of chromium, the chromium is in a trivalent positive state. Thus, when the term ionic chromium is utilized herein, trivalent positive chromium, i.e., $Cr^{+++}$, is especially contemplated. In fact, ionic forms of chromium wherein the chromium is in a negatively charged anion provided substantially no alumina removal from alumina-containing materials when treated under the aforementioned refluxing conditions.

In carrying out the dealuminization pursuant to the present invention, it is important to utilize a high ratio of $Cr^{+++}$ to aluminum in the solid being treated. It has been found that the atomic ratio of chromium in the solution to aluminum in the material being treated should be greater than 0.5. Lesser ratios do not give any significant dealuminization as revealed in the examples herein.

Further, the pH of the solution of chromium cations must be less than 3.5 in order to achieve worthwhile results in accordance with the process of this invention.

Specifically contemplated chromium salts include $CrCl_3$, $Cr(NO_3)_3$, $CrK(SO_4)_2$ and $CrBr_3$. It has been found that by employing a chromium salt under the aforementioned conditions, especially by refluxing the chromium salt with the crystalline aluminosilicate material, the porosity of materials can be substantially and remarkably changed. Thus, dense zeolites such as erionite can have their sorption capacity and pore diameter substantially changed. The aperture opening for erionite is about 5 Angstroms and in its as received state it sorbs less than 2.0 weight percent cyclohexane at 25°C. and 20 mm Hg. By refluxing a naturally obtained erionite sample with aqueous $CrCl_3$, its sorption capacity can be remarkably affected. Indeed, it has also been found that the dealuminized erionite sample sorbs at least 2.5 weight percent, e.g., 3.7 weight percent cyclohexane. Its pore diameter increases to at least 5.5 Angstroms. This sample can subsequently undergo desilication whereby its cyclohexane sorption is greater than 6.0 weight percent determined under the conditions above specified. In such case, the water sorption and n-hexane sorption properties are also improved with increase in the surface area without substantially any adverse effects of the crystallinity of the material.

It has also been found that when clinoptilolite in its as received state is refluxed with a chromium salt solution of the mineral acid, its pore diameter can be increased from a value of about 3.5 to greater than 4 and its sorption properties improved such that it sorbs at least 1.5 weight percent cyclohexane determined at 25°C. under 20 mm Hg. pressure. Similarly, phillipsite, initially having a pore diameter of about 4.0 Angstroms, can be so modified by treatment with a chromium salt solution that its pore diameter is at least 5.0 Angstroms and it becomes capable of sorbing at least 1.5 weight percent cyclohexane at 25°C. and 20 mm Hg. Concomitantly, these materials become more useful for gas oil cracking especially in an ion exchanged form as will be seen from the data below.

Dealuminization has heretofore been performed employing either an acid or a chelating agent such as ethylenediaminetetraacetic acid (hereinafter EDTA). However, the use of chromium chloride solution in the manner of this invention has been found to provide a substantially better weight percent removal of alumina than provided by treatment with an acid, e.g., hydrogen chloride. The chromium treatment is superior to EDTA treatment in that the resultant material is more porous. When zeolites were dealuminized and desilicated as explained below, it was found that both the n-hexane and cyclohexane sorption capacities increased after silica removal, in sharp contrast to the decreased sorption capacity after alumina removal by EDTA followed by silica removal.

Generally speaking, the amount of chromium salt solution used relative to the amount of crystalline aluminosilicate material being treated can vary widely. Many factors affect the selection of the relative amounts including the concentration of the chromium salt in the solution, temperature to be employed, the duration of the treatment, the degree of dealuminization desired and the specific material being treated. As a generalization, between 10 and 50 milliliters of salt solution are employed per gram of material being treated. The treatment at refluxing conditions is generally performed over a period of time ranging from ½ to 24 hours in which case the degree of alumina removal, depending on the amount of chromium in solution, is between 5 and 80 percent. Dealuminization can be performed on the materials in their as synthesized or as received states. In the case of aluminosilicate materials to be ion exchanged, the material can be treated with the chromium salt solution first, then ion exchanged or it can be initially ion exchanged, then dealuminized with the chromium salt solution as above set forth. Furthermore, dealuminization and ion exchange can be performed simultaneously by employing a single solution containing the chromium salt of the mineral acid and a salt, the cation of which is desired to be ionically exchanged for the cations of the aluminosilicate material.

While not wishing to be bound by any theory, it is believed that the alumina removal from crystalline aluminosilicates is a second step following an initial exchange of the chromium ions for ions of the alumina containing substance. Subsequent treatment at high temperatures in the presence of excess chromium salts and water effectuates removal of the alumina from the framework which combines with the chromium present. Alumina is removed from the substance during which time a portion of the chromium goes into a non-exchanged position, i.e., it does not satisfy the electronegativity of the remaining alumina. This is substantiated by data obtained by refluxing an aqueous chromium chloride solution with faujasite. It was found that up to 6 weight percent chromium could be incorporated into the faujasite in a non-exchangeable form. Subsequent catalytic evaluations of this material in a rare earth exchanged form but containing the chromium revealed substantially the same excellent cracking activity and selectivity as the rare earth form without chromium, but with oxidation properties enabling its use in the conversion of carbon monoxide to carbon dioxide during catalytic regeneration. Such solves a number of the problems which occur in cyclic cracking processes where the incomplete combustion of the coke affects the entire process.

Experimental results revealed that the effect of contact time of the aqueous solution of chromium salt from 1 to 24 hours with varying normality from 0.5 to 2.0 does not change the degree of alumina removal substantially. However, an increase in the volume of aqueous chromium salt solution appreciably affects the rate of alumina removal although the relationship is not linear. At low alumina removals, the ratio of chromium to aluminum atoms removed is 5/1. At higher alumina removals, the ratio increases to 10/1 and higher although not all crystalline aluminosilicate materials behave identically.

DESILICATION

Dealuminized crystalline aluminosilicate materials can be desilicated to remove silica from the composition. Thus, it has been found that by contacting the dealuminized material with an alkali metal salt or ammonium salt, silica can be removed from the material without adversely affecting the crystallinity of the substance being treated. For example, a dealuminized natural erionite having, say, 30 percent of its alumina removed, can be desilicated to thus open up the porous structure so that it sorbs materials not appreciably sorbed without the dealuminization-desilication treatment. The silica is removed usually from the channels or pores of the porous material or from the surface. Thus, erionite, for instance, in untreated form having a pore diameter of about 5 Angstroms can be dealuminized by the aforesaid chromium salt treatment and then subsequently desilicated such that its pore diameter is increased to at least 5.5 Angstroms. In so doing, the material is rendered substantially more porous and its cyclohexane sorption increases from about 2 weight percent to greater than 4 weight percent and generally greater than 6 weight percent determined at 25°C. and 25 mm Hg. The relative amounts of alkali metal or ammonium salt employed, their normality, the duration of contact, the temperature of the solutions are not particularly critical in desilication after dealumination in accordance with the present invention. Generally speaking, a solution having a normality between 0.1 and 10.0 will be suitable. The degree of contact and the normality are generally correlated to the degree of silica removal desired bearing in mind that the silica being removed is silica which had previously been bonded to tetrahedral alumina in the crystal framework. Particularly suitable alkali metal and ammonium salts useful for this purpose include sodium chloride, sodium bromide, sodium sulfate, potassium chloride, potassium nitrate, lithium chloride, ammonium chloride, ammonium sulfate. If desired, an ammonium salt solution can be employed to effect removal of some of the occluded silica and ion exchange of at least a portion of the cations satisfying the electronegative charge of remaining aluminum in the structure, i.e., the tetrahedra in the case of a crystalline aluminosilicate zeolite.

HYDROCARBON CONVERSION

Using the preparative techniques described above, important and valuable catalytic substances can be prepared. For instance, as noted above, a synthetic faujasite of the Y variety can be dealuminized by chromium salt treatment of this invention. The chromium salt treatment can occur before, after or during ion exchange of the zeolite to remove originally contained alkali metal cations. The substance has been found to have exceptionally good catalytic uses. Based on gasoline selectivity and cracking activity of gas oils, it has been found that a steamed chromium salt treated dealuminized REY catalyst compares quite favorably to a steamed REY catalyst in cracking performance. The dealuminized material has the advantage over the REY catalyst of having high oxidation activity useful in promoting the conversion of CO to $CO_2$ during the regeneration cycle of the cracking process.

This new technique enables the incorporation of an oxidation component into the molecular sieve component of a cracking catalyst without any adverse effect on its catalytic cracking properties. This oxidation component may be added either before or after or at the same time as the rare earth exchange of the molecular sieve. Thus, instead of adding a small amount of oxidation promoter into the amorphous matrix of the cracking catalyst, large amounts of oxidation promoter in the form of complexing chromium can be incorporated into the active molecular sieve material.

In order to more fully illustrate the nature of the present invention and the manner of practicing the same, the following examples are presented:

EXAMPLE 1

A natural erionite material obtained from Mt. Moses, Nevada and shown by X-ray to contain 20 percent clinoptilolite was employed for several treatments with a 1 Normal $CrCl_3$ solution (pH 2.1) for the purpose of dealuminizing the zeolite. In each case the $CrCl_3$ was refluxed through the erionite. The temperature of the treatment was about 100°C. and the chromium to aluminum atomic ratio varied from 0.8 to 16.4, and times from 2 to 24 hours (Details in Table 4). Samples of erionite were withdrawn and the degree of alumina removal and the crystallinity of the sample was determined. Set forth below in Table 1 is a comparison of the degree of alumina obtained and the crystallinity of the sample over the various periods of refluxing.

TABLE 1

| Alumina removed — | None | 8 | 20 | 38 | 44 | 64 |
|---|---|---|---|---|---|---|
| Crystallinity, % — | 80 | 80 | 85 | 70 | 65 | 35 |

The crystallinity was based upon the crystallinity of a standard. It should be noted that no crystallinity loss occurred until about 40 percent of the alumina was removed.

The 38 percent dealuminized sample was refluxed with 150 ml. per gram of 1.0 N NaCl for 1 hour, filtered, and the procedure repeated two more times, removing 16 percent silica. Sorption capacity in surface area increased by both the dealuminization and the desilication provided by the sodium salt treatment. The data for the various samples is set forth in the table below. The water sorption was determined at 12 mm Hg and 25°C. and the normal hexane and the cyclohexane was determined at 20 mm Hg and 25°C.

TABLE 2

| | Sorption, Wt.% | | | S.A., | |
|---|---|---|---|---|---|
| | $H_2O$ | n-hexane | Cyclo-hexane | $m^2/g$ | Crystallinity |
| Erionite | 13.3 | 5.2 | 1.7 | 286 | 80 |
| Dealuminized | 16.6 | 9.4 | 3.7 | 371 | 70 |
| Then Desilicated | 17.9 | 10.7 | 6.8 | 408 | 70 |

The surface area was determined by the Brunauer-Emmet-Teller Procedure using nitrogen at $-195°C$.

EXAMPLE 2

10 Grams of a phillipsite-clinoptilolite composition was refluxed with 600 ml. of 1.0 Normal $CrCl_3$ solution (pH 2.1) for 2 hours at about 100°C. where the chromium to aluminum atomic ratio was 7.9. (Details in Table 10). Upon analysis, it was found that 41 percent of the alumina was removed. A 4g. portion of this sample was thereafter desilicated by contacting it with 600 ml. of 1.0 normal aqueous solution for NaCl for 1 hour, total of three contacts. In the table below, there is set forth the composition of the untreated material and its sorption properties as well as the composition after each of the above specified treatments.

TABLE 3

PHILLIPSITE-CLINOPTILOLITE
DESILICATION FOLLOWING DEALUMINIZATION

| | | Step 1 Aluminum Removal | Step 2 Silicon Removal |
|---|---|---|---|
| % Removal | | 41 | 14 |
| Washed, Dried Catalyst | Untreated | | |
| Analyses, Wt. % | | | |
| K | 0.90 | 0.92 | 0.16 |
| Na | 5.0 | 0.84 | 3.7 |
| Mg | 3.90 | 1.8 | 2.42 |
| $SiO_2$ | 64.6 | 76.5 | 73.4 |
| $Al_2O_3$ | 16.2 | 11.4 | 12.7 |
| Fe | 0.77 | 2.07 | 2.42 |
| Cr | — | 0.63 | — |
| Ash | 80 | 88.5 | 87.0 |
| $SiO_2/Al_2O_3$ Ratio | 6.8 | 11.4 | 8.0 |
| Eq. K/Al | 0.07 | 0.11 | 0.02 |
| Eq. Na/Al | 0.74 | 0.16 | 0.64 |
| Eq. Mg/Al | 1.02 | 0.67 | 0.87 |
| n-Hexane Adsorption, Wt. % | 0.9 | 3.2 | 4.5 |
| Cyclohexane Adsorption, Wt.% | 0.8 | 4.0 | 5.6 |

EXAMPLE 3

Several samples of a natural erionite containing clinoptilolite were treated in different ways with a $CrCl_3$ solution. Various treatments and the properties of the resultant products compared with the untreated material are set forth in Table 4.

TABLE 4

TREATMENT OF ERIONITE WITH $CrCl_3$ — DETAILS

| | | | | | | | |
|---|---|---|---|---|---|---|---|
| 1.0 N. $CrCl_3$, ml | | 120 | 600 | 1200(×2) | 600(×3) | 600(×3) | 1200 |
| Erionite g. | | 20 | 20 | 40 | 20 | 20 | 4 |
| Contact Time (Reflux) Hrs. | | 2 | 2 | 2(×2) | 2(×3) | 24(×3) | 1 |
| Contact Temperature, (approx.) °C. | | 100 | 100 | 100 | 100 | 100 | 100 |
| No. of Contacts | | 1 | 1 | 2 | 3 | 3 | 1 |
| Ratio of Cr in Solution/Al in zeolite | | 0.8 | 4.1 | 8.2 | 16.4 | 16.4 | 41.0 |
| Washed, Dried Catalyst g. | | 16.9 | 15.0 | 27.6 | 13.5 | 12.7 | 3.2 |
| Analyses Wt% | | | | | | | |
| | Untreated | | | | | | |
| K | 3.7 | 3.93 | 3.4 | 2.1 | 1.82 | 1.25 | 1.8 |
| Na | 3.3 | 0.80 | 0.25 | 0.07 | 0.05 | 0.05 | 0.05 |
| Ca | 3.0 | 2.66 | 0.90 | 0.57 | — | — | 0.52 |

TABLE 4-continued
TREATMENT OF ERIONITE WITH $CrCl_3$ — DETAILS

| | | | | | | | |
|---|---|---|---|---|---|---|---|
| Mg | 0.57 | 0.4 | 0.54 | 0.41 | — | 0.31 | 0.43 |
| $SiO_2$ | 66.8 | 73.4 | 75.1 | 80.6 | 82.2 | 86.6 | 80.5 |
| $Al_2O_3$ | 15.4 | 15.5 | 13.8 | 11.6 | 10.6 | 7.1 | 12.0 |
| Fe | 1.95 | 2.30 | 2.12 | 2.0 | 1.56 | 2.05 | 1.98 |
| Cr | — | 0.21 | 0.16 | 0.17 | 0.30 | 0.42 | 0.35 |
| Ash | 81.1 | 86.2 | 93.2 | 90.1 | 83.6 | 84.5 | 89.0 |
| Aluminum Removal, Wt. % | — | 8 | 20 | 38 | 44 | 64 | 35 |
| $SiO_2/Al_2O_3$ Ratio | 7.3 | 8.0 | 8.3 | 11.8 | 13.2 | 23.9 | 11.4 |
| Eq. K/Al | 0.31 | 0.33 | 0.20 | 0.24 | 0.22 | 0.23 | 0.20 |
| Eq. Na/Al | 0.48 | 0.11 | 0.04 | 0.01 | 0.01 | 0.02 | 0.01 |
| Eq. Ca/Al | 0.50 | 0.44 | 0.15 | 0.13 | — | — | 0.11 |
| Eq. Mg/Al | 0.16 | 0.11 | 0.15 | 0.15 | — | 0.19 | 0.15 |
| n-Hexane Adsorption, Wt. % | 5.2 | 5.7 | 7.5 | 9.4 | 8.2 | 9.6 | — |
| Cyclohexane Adsorption, Wt. % | 1.7 | 2.2 | 2.7 | 3.7 | 5.8 | 7.4 | — |
| Crystallinity | | | | | | | |
| % Erionite | 80 | 80 | 85 | 70 | 65 | 45 | — |
| % Clinoptilolite | 20 | 35 | 35 | 40 | 30 | 35 | — |

From the table above, it will be seen that both the normal hexane and cyclohexane properties are improved from values of 5.2 to 9.6 and 1.7 to 7.4 weight percent respectively indicating utility of the treated material for cracking gas oils.

EXAMPLE 4

Two samples of a natural erionite were treated, one with a refluxing 1.0 normal aqueous $CrCl_3$ solution and the other with a 0.01 N aqueous refluxing HCl solution. A summary of the two treatments is set forth in Table 5 below:

TABLE 5

| | Erionite | | | |
|---|---|---|---|---|
| Solution | 1.0 N $CrCl_3$ | | 0.01 N HCl | |
| pH | 2.1 | | 1.9 | |
| cc/g Catalyst | 6 | 30 | 30(×2) | 150(×4) |
| Contact Temperature (approx) °C. | 100 | 100 | 100 | 100 |
| Reflux Time, hrs. | 2 | 2 | 2 | 20 |
| Number of Contacts | 1 | 1 | 2 | 4 |
| % Aluminum Removed | 8 | 20 | 38 | 2 |

Contact of erionite with 30 volumes of refluxing 1.0 N $CrCl_3$ (pH 2.1) for 2 hours removed 20 percent aluminum. Two such treats removed 38 percent aluminum. In contrast, contact of the erionite with 600 volumes of refluxing 0.01 N HCl (pH 1.9) in 4 treats, 20 hours each, removed only 2 percent aluminum. If the comparison is made on equal halide content, aluminum removal with $CrCl_3$ (6 volumes refluxing 1.0 N $CrCl_3$ for 2 hours) is 8 percent vs. 2 percent for the HCl (600 volume refluxing 0.01 N HCl, and much longer contact time).

Aluminum was also removed more easily from zeolite T prepared pursuant to U.S. Pat. No. 2,950,952 with $CrCl_3$ than with HCl.

TABLE 6

| Solution | 1.0 N $CrCl_3$ | | 0.01 N HCl | |
|---|---|---|---|---|
| pH | 2.1 | | 1.9 | |
| cc/g Catalyst | 300 | 300 | 300 | 300 |
| Contact Temperature (approx.) °C. | 100 | 100 | 100 | 100 |
| Reflux Time, minutes | 10 | 60 | 10 | 60 |
| % Aluminum Removed | 15 | 89 | nil | 4 |

EXAMPLE 5

40 Grams of a natural erionite containing clinoptilolite was dealuminized by contacting with 1200 ml. of an aqueous solution of 1.0 N normal $CrCl_3$ (pH 2.1) at refluxing conditions for 2 hours, two contacts, the contact temperature being about 100°C. Thereafter a portion of it was desilicated by refluxing the dealuminized erionite with 150 ml. of a 1.0 N NaCl solution 3 times, each for an hour. 16 percent of the silica of the original sample was removed. Another portion was treated in the same manner with 1.0 N $NH_4Cl$, removing 15 percent of the silica. A portion of the dealuminized desilicated (NaCl) erionite was thereafter refluxed 4 times for an hour with 20 ml. 1.0 $NH_4Cl$ aqueous solution. The data summarizing the resultant product is set forth in Table 7 below:

TABLE 7
ERIONITE - DESILICATION FOLLOWING DEALUMINIZATION

| | Original Erionite | De-Aluminized | Then De-Silicated NaCl | Then De-Silicated $NH_4Cl$ | Then $NH_4Cl$ Exchanged After NaCl |
|---|---|---|---|---|---|
| $SiO_2/Al_2O_3$ Ratio | 7.3 | 11.8 | 9.9 | 10.1 | 10.0 |
| Fe Content, Wt. % | 1.95 | 2.0 | 2.12 | 2.3 | 2.1 |
| Cr Content, Wt. % | — | 0.17 | 0.18 | 0.15 | 0.19 |
| Equivalents K/Al | 0.31 | 0.24 | 0.17 | 0.16 | 0.18 |
| Na/Al | 0.48 | 0.01 | 0.63 | 0.01 | 0.01 |
| Ca/Al | 0.50 | 0.13 | 0.03 | 0.03 | 0.03 |
| Mg/Al | 0.16 | 0.15 | 0.07 | 0.04 | 0.06 |
| $NH_4$/Al(By Diff.) | — | — | — | 0.76 | 0.63 |
| Total | 1.45 | 0.53 | 0.90 | 1.00 | 1.00 |
| Adsorptions, Wt. % (20 mm Press., Equilibrium, Room Temp.) | | | | | |
| $H_2O$ | 13.3 | 16.6 | 17.9 | — | — |
| n-Hexane | 5.2 | 9.4 | 10.7 | 8.2 | 9.4 |
| Cyclohexane | 1.7 | 3.7 | 6.8 | 9.2 | 7.7 |
| Surface Area, $m^2/g$ | 286 | 371 | 408 | — | — |
| Crystallinity, % Erionite | 80 | 70 | 70 | 85 | 90 |
| % Clinoptilolite | 20 | 40 | 30 | 40 | 35 |

EXAMPLE 6

Several samples of zeolite T were refluxed for different periods of time with a 1.0 N $CrCl_3$ solution. Other samples of zeolite T were refluxed with varying concentrations of the $CrCl_3$ solution. Still other samples were given single and stepwise treatment of $CrCl_3$ solution at reflux. Table 8 set forth below summarizes the effects of time, normality and methods of treatment with respect to the weight percent alumina removed.

EXAMPLE 7

Several samples of zeolite T were refluxed for 1 hour (temperature approx. 100°C.) with different chromium salt solutions each of which was a 1.0 normal solution. 15 ml. solutions were employed per gram of zeolite T. Set forth in Table 9 below is a summary of the analysis and sorption properties of resultant materials compared with the untreated material.

TABLE 8

VARIABLES
TREATMENT OF ZEOLITE T WITH $CrCl_3$

1. Effect of Time (Reflux)

| ml. 1.0 N $CrCl_3$/g T | Time, Hrs. | % Aluminum Removed |
|---|---|---|
| 15 | 1 | 28 |
| 15 | 6 | 27 |
| 15 | 24 | 32 |

2. Effect of Normality (Reflux)

| Normality | ml/g T | Time, Hrs. | % Aluminum Removed |
|---|---|---|---|
| 0.5 (2.5 pH) | 30 | 1 | 22 |
| 1.0 (2.1 pH) | 15 | 1 | 28 |
| 2.0 (1.9 pH) | 7.5 | 1 | 28 |

3. Effect of Amount of $CrCl_3$ (Reflux)

a. Single Treats

| Normality | ml/g T | Time, Hrs. | Ratio of Cr in Solution to Al in Zeolite | % Aluminum Removed |
|---|---|---|---|---|
| 1.0 | 7.5 | 6 | 0.8 | 15 |
| 1.0 | 15 | 6 | 1.5 | 27 |
| 2.0 | 7.5 | 1 | 1.5 | 28 |
| 2.0 | 30 | 1 | 6.2 | 70 | b. Stepwise Treats

| Normality | ml/g T | Time, Hrs. | Ratio of Cr in Solution to Al in Zeolite | % Aluminum Removed |
|---|---|---|---|---|
| 1.0 | 15 | 1 | 1.5 | 28 |
| 1.0 | 15 + 12 | 1 + 1 | 1.5 + 1.7 | 40 |

TABLE 9

COMPARISON OF CHROMIUM SALTS

| Solution | | 1.0 N $CrCl_3$ | 1.0 N $Cr(NO_3)_3$ | 1.0 N $CrK(SO_4)_2$ |
|---|---|---|---|---|
| pH | | 2.1 | 2.3 | 2.7 |
| cc | | 600 | 600 | 600 |
| Zeolite T, g. | | 40 | 40 | 40 |
| Contact Time (approx. 100°C.), Hrs. | | 1 | 1 | 1 |
| Washed, Dried Catalyst, g. | | 31.6 | 32.1 | 36.1 |
| Analyses, Wt.% | Untreated | | | |
| K | 11.3 | 7.3 | 6.63 | 10.7 |
| Na | 2.3 | 0.24 | 0.24 | 0.17 |
| $SiO_2$ | 65.3 | 74.0 | 74.5 | 69.3 |
| $Al_2O_3$ | 18.5 | 15.2 | 15.1 | 15.9 |
| Cr | — | 0.91 | 1.0 | <0.2 |
| Ash | 83.3 | 90.6 | 88.8 | 90.2 |
| Aluminum Removal, Wt.% | — | 28 | 28 | 19 |
| $SiO_2/Al_2O_3$ Ratio | 6.0 | 8.3 | 8.4 | 7.4 |
| Eq. K/Al | 0.73 | 0.63 | 0.57 | 0.88 |
| Eq. Na/Al | 0.28 | 0.03 | 0.04 | 0.02 |
| n-Hexane Adsorption, Wt.% | 6.3 | 7.5 | 7.6 | 5.0 |
| Cyclohexane Adsorption, Wt. % | 2.1 | 2.1 | 3.4 | 3.8 |

EXAMPLE 8

Set forth in Table 10 is a comparison of the ease of aluminum removal from zeolites by refluxing the zeolite with a 1.0 N aqueous $CrCl_3$. The duration of refluxing was as indicated in Table 10 below.

TABLE 10
COMPARISON OF EASE OF ALUMINUM REMOVAL FROM DENSE ZEOLITES WITH 1.0 N $CrCl_3$

| Zeolite | T | Erionite | Phillipsite-Clinoptilolite | Na Mordenite | ZSM-4 |
|---|---|---|---|---|---|
| $Al_2O_3$ Content, Wt. % | 18.5 | 15.4 | 16.2 | 11.4 | 11.2 |
| $SiO_2/Al_2O_3$ Ratio | 6.0 | 7.3 | 6.8 | 11.9 | 12.6 |
| 1.0 N $CrCl_3$, Reflux, Hrs. | 1 | 2 | 2 | 2 | 1 |
| cc/g. | 15 | 30 | 60 | 30 | 15 |
| Ratio, Cr in Sol/Al in cat. | 1.7 | 4.1 | 7.9 | 5.2 | 3.6 |
| % Aluminum Removed | 28 | 20 | 41 | 7 | — |
| $SiO_2/Al_2O_3$ Ratio | 8.3 | 8.3 | 11.4 | 12.9 | 12.8 |
| Cr, Wt. % | 0.91 | 0.16 | 0.63 | 0.27 | 0.54 |
| Adsorption, n-Hexane | 7.5 | 7.5 | 3.2 | 5.7 | 4.4 |
| Cyclohexane | 3.2 | 2.7 | 4.0 | 7.2 | 4.5 |

It will be noted that the ZSM-4 zeolite was quite resistant to alumina removal with the treatment conditions employed. The increase in its silica to alumina mole ratio was slight i.e., 12.6 to 12.8.

EXAMPLE 9

In order to determine the effects of temperature of the chromium salt solution on the sodium form of zeolite Y, several comparative experiments were performed and the results are itemized in Table 11 below:

It should be stated that in each case of chromium salt solution treatment, the material was filtered and washed until anion free. Thereafter it was generally dried at 100°C. Such complete washing procedure is generally recommended to prevent the volatilization of undesirable components, for example the volatilization upon calcination of chromium oxychlorides, which is formed when excess $CrCl_3$ is not completely washed out of the treated zeolite.

EXAMPLE 10

In illustration of the requirement that the crystalline aluminosilicate treated in accordance with this invention must have a silica/alumina mole ratio of between greater than 3 and about 12, the same analysis as out-

TABLE 11

| | STARTING ZEOLITE | | | | | | | |
|---|---|---|---|---|---|---|---|---|
| NaY, g. | | 50 | 100 | 50 | 20 | 20 | 20 | 20 |
| 1.0 N $CrCl_3$ Solution, ml. | | 750 | 1500 | 750 | 600 | 600(×2) | 600 | 600(×2) |
| Ratio, Cr in Sol/Al in Cat. | | 1.5 | 1.5 | 1.5 | 2.9 | 5.9 | 2.9 | 5.9 |
| Temperature, (approx.)°C. | | 100 | 100 | 100 | 100 | 100 | 25 | 25 |
| Contact Time, hr. | | 0.5 | 2 | 24 | 2 | 2(×2) | 2 | 2(×2) |
| Number of Contacts | | 1 | 1 | 1 | 1 | 2 | 1 | 2 |
| Washed, Dried Cat.,g. | | 43.4 | 95.6 | 42.2 | 15.0 | 11.1 | 19.2 | 18.3 |
| Analysis, Wt.% | | | | | | | | |
| $SiO_2$ | 63.6 | 71.4 | 71.6 | 74.0 | 81.5 | 96.8 | 66.9 | 67.4 |
| $Al_2O_3$ | 21.2 | 16.7 | 16.1 | 14.0 | 10.4 | 1.35 | 21.6 | 21.2 |
| Na | 8.55 | 1.4 | 1.7 | 1.4 | 0.95 | 0.02 | 3.14 | 2.34 |
| Cr | — | 6.4 | 7.1 | 7.0 | 4.9 | 1.04 | 4.8 | 4.8 |
| Ash | 82.2 | 84.4 | 81.8 | 83.8 | 82.3 | 87.8 | 81.3 | 81.1 |
| Alumina Removal, wt.% | — | 30 | 32 | 43 | 62 | 96 | 3 | 6 |
| $SiO_2/Al_2O_3$ Ratio | 5.1 | 7.3 | 7.6 | 9.0 | 13.3 | 122 | 5.4 | 5.4 |
| Eq. Na/Al | 0.89 | 0.19 | 0.24 | 0.22 | 0.20 | 0.03 | 0.32 | 0.25 |
| n-Hexane Adsorption, Wt.% | 17.5 | 9.3 | 11.0 | 13.7 | 11.0 | 12.9 | 12.6 | 10.6 |
| Cyclohexane Adsorption, Wt.% | 15.4 | 8.9 | 14.1 | 17.8 | 11.8 | 13.0 | 15.3 | 12.2 |

It is noted that alumina removal occurred at reflux (100°C) in every case. However, at room temperature, alumina was not removed from the zeolite as indicated by the $SiO_2$ ratio. The $CrCl_3$ treatment at room temperature had effected the exchange of chromium ions into the zeolite as taught by prior art.

lined in Table 11 for zeolite Y (silica/alumina ratio between 3 and 6) was conducted on zeolite X (silica/alumina ratio of 2.5 ± 0.5). That analysis appears in Table 12, following. Note that the crystallinity of the zeolite X is destroyed and an amorphous product is obtained.

TABLE 12

| | Starting Zeolite | | |
|---|---|---|---|
| Zeolite X, g. | | 50 | 50 |
| $CrCl_3$ Solution Normality | | 1.0 | 0.5 |

TABLE 12-continued

| | | |
|---|---|---|
| Volume of solution, ml. | 750 | 750 |
| Atomic Ratio, Cr. in Sol./Al in zeolite | 0.8 | 0.4 |
| Temperature (approx.) °C. | 100 | 100 |
| Contact Time, Hrs. | 2 | 2 |
| Number of Contacts | 1 | 1 |
| Washed, Dried Cat., g. | 10.8 | 54.6 |
| Analysis, Wt.% | | |
| SiO$_2$ | 60.7 | 48.4 |
| Al$_2$O$_3$ | 22.0 | 31.8 |
| Na | 0.06 | 0.11 |
| Cr | 13.2 | 12.7 |
| Ash | — | 79.6 |
| Aluminum Removal | 46 | 2 |
| SiO$_2$/Al$_2$O$_3$ Ratio | 4.7 | 2.6 |
| Eq. Na/Al | 0.01 | 0.01 |
| n-Hexane Adsorption, Wt.% | 5.9 | — |
| Cyclohexane Adsorption, Wt.% | — | 8.6 |
| Crystallinity, X-ray | Amorphous | Amorphous |

(Original column showing: SiO$_2$ 48.7, Al$_2$O$_3$ 32.8, Na 14.9, Ash 81.7, SiO$_2$/Al$_2$O$_3$ Ratio 2.5, Eq. Na/Al 1.01, n-Hexane Adsorption 15.8, Cyclohexane Adsorption 18.2, Crystallinity 100)

Observe also that, aside from the fact that the crystallinity of the zeolite X was destroyed, there was a drastic decrease in the amount of alumina removed when the atomic ratio of Cr to Al was dropped below 0.5 (e.g., 0.4).

EXAMPLE 11

Several forms of a dealuminized lanthanum exchanged form of zeolite Y were prepared by different techniques. One involved treatment with a 15 ml. per gram zeolite 1.0 normal aqueous solution of CrCl$_3$ followed by ion exchange with a 1.0 normal aqueous solution of LaCl$_3$. Another such treatment involved initial exchange with the LaCl$_3$ solution then dealuminization with the refluxing solution of CrCl$_3$, 15 ml. per gram zeolite. A third exchange involved refluxing a mixed solution involving CrCl$_3$ and LaCl$_3$. The CrCl$_3$ refluxing in each case was performed for 24 hours. A comparison of the resultant products against the original non-dealuminized sodium zeolite Y is set forth in Table 13.

TABLE 13

| | Original NaY | CrCl$_3$ then LaCl$_3$ | LaCl$_3$ then CrCl$_3$ | Single Solution CrCl$_3$ + LaCl$_3$ |
|---|---|---|---|---|
| SiO$_2$, Wt. % | 63.6 | 71.4 | 71.6 | 66.0 |
| Al$_2$O$_3$, Wt. % | 21.2 | 14.5 | 13.1 | 12.4 |
| Na, Wt. % | 8.55 | 0.91 | 0.46 | 1.36 |
| Cr, Wt. % | — | 6.36 | 4.8 | 4.1 |
| La, Wt. % | — | 4.6 | 6.05 | 3.54 |
| SiO$_2$/Al$_2$O$_3$ Ratio | 5.1 | 8.4 | 9.3 | 9.0 |
| % Alumina Removal | — | 37 | 45 | 43 |

Several different dealuminized forms of zeolite Y were prepared by contacting the zeolite Y in a sodium form for varying periods of time with an aqueous solution of CrCl$_3$ under refluxing conditions. A portion of the dealuminized zeolite Y in each case was back exchanged with a 1.0 N NaCl aqueous solution. The exchange comprised 3 refluxing operations, each of which was for one hour and utilized 300 ml. solution per gram zeolite. The various compositions of the dealuminized back sodium exchanged zeolite Y compositions are indicated in Table 14 below:

TABLE 14

BACK EXCHANGE WITH 1.0 N NaCl

| | Cr [−32% Al] Y | | Cr [−43% Al] Y | | Cr [−62% Al] Y | | Cr [−96% Al] Y | |
|---|---|---|---|---|---|---|---|---|
| | As Is | After Ex.* | As Is | After Ex. | As Is | After Ex. | As Is | After Ex. |
| SiO$_2$, Wt. % | 71.6 | 67.6 | 74.0 | 72.5 | 81.5 | 78.8 | 96.8 | 96.0 |
| Al$_2$O$_3$, Wt. % | 16.1 | 16.6 | 14.0 | 14.8 | 10.4 | 12.1 | 1.35 | 2.4 |
| Na, Wt. % | 1.7 | 4.09 | 1.4 | 3.7 | 0.95 | 3.0 | 0.02 | 0.16 |
| Cr, Wt. % | 7.1 | 5.68 | 7.0 | 5.93 | 4.9 | 5.33 | 1.04 | 1.40 |
| SiO$_2$/Al$_2$O$_3$, Ratio | 7.6 | 6.9 | 9.0 | 8.4 | 13.3 | 11.1 | 122 | 68 |
| Equivalents Na/Al | 0.24 | 0.55 | 0.22 | 0.55 | 0.20 | 0.55 | 0.03 | 0.15 |
| Catalyst Identification Number | 1A | | 2A | | 3A | | 4A | |

*125 ml/g

Another portion of the same dealuminized but not back exchanged zeolite Y was given 3 similar ion exchange treatments with an aqueous 1.0 N NH$_4$Cl solution. The composition of the various resultant materials is set forth in Table 15 below:

TABLE 15

BACK EXCHANGE WITH 1.0 N NH$_4$Cl

| | Cr [−32% Al] Y | | Cr [−43% Al] Y | | Cr [−62% Al] Y | | Cr [−96% Al] Y | |
|---|---|---|---|---|---|---|---|---|
| | As Is | After Ex. | As Is | After Ex. | As Is | After Ex. | As Is | After Ex. |
| SiO$_2$, Wt. % | 71.6 | 73.5 | 74.0 | 76.8 | 81.5 | 81.8 | 96.8 | 95.9 |
| Al$_2$O$_3$, Wt. % | 16.1 | 18.6 | 14.0 | 16.0 | 10.4 | 13.0 | 1.35 | 2.3 |
| Na, Wt. % | 1.7 | 0.07 | 1.4 | 0.07 | 0.95 | 0.06 | 0.02 | 0.05 |

TABLE 15-continued

| | BACK EXCHANGE WITH 1.0 N NH₄Cl | | | | | | | |
|---|---|---|---|---|---|---|---|---|
| | Cr [−32% Al] Y | | Cr [−43% Al] Y | | Cr [−62% Al] Y | | Cr [−96% Al] Y | |
| | As Is | After Ex. | As Is | After Ex. | As Is | After Ex. | As Is | After Ex. |
| Cr, Wt. % | 7.1 | 6.36 | 7.0 | 6.73 | 4.9 | 5.44 | 1.04 | 1.38 |
| N, Wt. % | — | 2.50 | — | 1.87 | — | 1.58 | — | 0.40 |
| SiO₂/Al₂O₃ Ratio | 7.6 | 6.2 | 9.0 | 8.2 | 13.3 | 10.7 | 122 | 71 |
| Equivalents Na/Al | 0.24 | 0.01 | 0.22 | 0.01 | 0.20 | 0.01 | 0.03 | 0.05 |
| N/Al | — | 0.49 | — | 0.43 | — | 0.44 | — | 0.59 |
| Catalyst Identification Number | | 1B | | 2B | | 3B | | 4B |

Another portion of the 33 percent by weight dealuminized zeolite Y was exchanged with an aqueous 1.0 N lanthanum chloride solution. The exchange comprised 3 refluxing operations, each of which was for 1 hour employing 35 ml. per gram zeolite. The resultant composition had the properties indicated in Table 16 below:

TABLE 16

| BACK EXCHANGE WITH 1.0 N LaCl₃ | | |
|---|---|---|
| | Cr [−43% Al] Y | |
| | As Is | After Exchange |
| SiO₂, Wt. % | 74.0 | 71.4 |
| Al₂O₃, Wt. % | 14.0 | 14.5 |
| Na, Wt. % | 1.4 | 0.91 |
| Cr, Wt. % | 7.0 | 6.36 |
| La, Wt. % | — | 4.6 |
| SiO₂/Al₂O₃ Ratio | 9.0 | 8.4 |
| Equivalents Na/Al | 0.22 | 0.14 |
| La/Al | — | 0.35 |
| Catalyst Identification Number | | 2C |

EXAMPLE 12

The various catalytic substances were calcined at 1000°F. for 16 hours and evaluated for the cracking of an East Texas light gas oil at 900°F. in a micro cat-c test. The weight and space velocities and catalyst to oil ratios are as reported in Table 17 below.

EXAMPLE 13

A fresh rare earth exchanged zeolite Y catalyst material was compared for its ability to oxidize carbon monoxide to carbon dioxide to another REY zeolite which had been dealuminized by treatment pursuant to this invention involving refluxing the zeolite with an aqueous solution of $CrCl_3$ prior to the rare earth exchange. The silica to alumina mole ratio of the $CrCl_3$ treated material was 8.4 (chromium content 6.36 weight percent) while the ratio of untreated material was 4.9. In Table 18 below there is set forth the oxidation abilities of the various materials at the temperatures specified. The carbon monoxide oxidation test was carried out by flowing a stream of 2 percent by volume carbon monoxide in air at 100 ml/min. over 1 cc. catalyst.

TABLE 18

| Temperature, °F. | Wt. % Oxidized to CO₂ | |
|---|---|---|
| | Fresh REY | Dealuminized REY |
| 450 | — | 7 |
| 500 | — | 55 |
| 550 | — | 92 |
| 600 | 2 | 97 |
| 650 | 4 | 100 |
| 700 | 9 | — |
| 750 | 54 | — |
| 800 | 100 | — |

TABLE 17

| E. TEXAS LGO CRACKING | | | | | | | | |
|---|---|---|---|---|---|---|---|---|
| | | | | | Product Distribution, Wt.% | | | |
| | Cat/Oil Ratio | WHSV | Conversion Wt. % | Selectivity, C₅ + Gaso. | C₁—C₃ | C₄ | Coke | C₅ + Gaso. |
| NaY | 2 | 3 | 33.5 | 73.4 | 7.0 | 5.0 | 14.6 | 24.6 |
| Cr[−32% Al]Y | 2 | 3 | 82.9 | 45.5 | 14.8 | 17.7 | 21.9 | 37.7 |
| NaCl Exchanged 1A | 2 | 3 | 76.6 | 46.7 | 12.1 | 13.2 | 27.9 | 35.8 |
| NH₄Cl Exchanged 1B | 2 | 3 | 36.1 | 56.8 | 12.3 | 13.8 | 16.1 | 20.5 |
| Cr[−43% Al]Y | 2 | 3 | 83.1 | 41.2 | 14.4 | 17.6 | 26.8 | 34.2 |
| NaCl Exchanged 2A | 2 | 3 | 75.2 | 44.9 | 12.0 | 12.0 | 31.1 | 33.8 |
| NH₄Cl Exchanged 2B | 2 | 3 | 74.7 | 31.9 | 21.2 | 18.8 | 28.1 | 23.8 |
| Cr[−62% Al]Y | 2 | 3 | 75.2 | 42.7 | 13.0 | 27.4 | 16.8 | 32.1 |
| NaCl Exchanged 3A | 2 | 3 | 70.7 | 51.5 | 11.0 | 12.5 | 25.0 | 36.4 |
| NH₄Cl Exchanged 3B | 2 | 3 | 49.5 | 50.2 | 13.9 | 14.8 | 21.1 | 24.8 |
| Cr[−96% Al]Y | 2 | 3 | 62.7 | 52.6 | 16.1 | 20.6 | 10.7 | 33.0 |
| NaCl Exchanged 4A | 2 | 3 | 29.6 | 61.9 | 12.1 | 11.1 | 14.9 | 18.3 |
| NH₄Cl Exchanged 4B | 2 | 3 | 54.8 | 47.1 | 17.5 | 15.5 | 19.9 | 25.8 |
| La Exchanged Cr[−43% Al]Y (2C) | 2 | 3 | 87.8 | 36.8 | 14.4 | 17.0 | 31.8 | 32.3 |
| Calcined 16 Hrs. at 950°F. | 2 | 3 | 91.3 | 42.9 | 12.6 | 21.3 | 23.0 | 39.2 |
| Steamed 24 Hrs. at 1200°F. | 2 | 3 | 86.1 | 63.9 | 10.4 | 18.8 | 7.0 | 55.0 |
| | 1 | 6 | 80.7 | 66.7 | 8.7 | 21.0 | 3.6 | 53.8 |
| | 0.2 | 30 | 64.0 | 79.0 | 6.2 | 14.3 | 0.5 | 50.6 |
| REY, Steamed 24 Hrs. at 1200°F. | 1 | 6 | 92.7 | 54.1 | 14.4 | 22.2 | 9.3 | 50.2 |
| | 0.2 | 30 | 78.6 | 75.4 | 7.3 | 15.7 | 1.7 | 59.3 |
| | 0.1 | 60 | 70.6 | 79.1 | 5.8 | 14.4 | 0.7 | 55.8 |

It will be seen that while the activity and selectivity did not compare favorably that after steaming it compared quite favorably to the standard REY material especially at the higher space velocities.

EXAMPLE 14

Several samples of 42 weight percent dealuminized REY catalyst containing 6.36 weight percent chromium were employed for the cracking of a Mid-Continent wide cut gas oil at 900°F. over a period of 10 minutes. Similarly, a REY catalyst material which had not been dealuminized was tested for cracking of the same material under the same conditions. In Table 19 below, there is set forth a comparison of the cracking activities of these two materials both fresh and after regeneration. It will be noted that the $C_5+$ gasoline selectivity compares quite favorably with the results obtained employing a non-dealuminized REY material. Bearing in mind the oxidation activity of this catalyst as shown from the table above, it is evident that it is a valuable cracking catalyst to maintain a favorable heat balance during catalytic cracking and regeneration steps normally employed.

EXAMPLE 15

In Table 20, set forth below, there is set forth the comparison of the cracking activity of various dense aluminosilicate zeolites and silica alumina. The cracking activity is expressed in the as is, i.e., the untreated form, the dealuminized form and the desilicated form. The extent of dealuminization and desilication is itemized. The table also presents the values obtained employing in one instance an erionite sample which was dealuminized, desilicated and ammonium exchanged.

TABLE 20

GAS OIL CRACKING*
WITH DE-ALUMINIZED AND DE-SILICATED ZEOLITES

| Catalyst | Conversion Wt. % | Selectivity $C_5+$ Gaso. | Yields $C_5+$ Gaso. | Dry Gas | $C_4$ | coke |
|---|---|---|---|---|---|---|
| Zeolite Phillipsite- | | | | | | |
| Clinoptilolite | | | | | | |
| As is | 4.5 | | | | | |
| De-aluminized 41% | 28.3 | 56.7 | 16.0 | 4.4 | 4.6 | 3.3 |
| Then De-silicated 14% | 20.0 | 66.9 | 13.4 | 2.0 | 2.1 | 2.6 |
| Zeolite T | | | | | | |
| As is | 5.3 | | | | | |
| De-aluminized 70% | 59.8 | 45.4 | 27.2 | 13.5 | 13.7 | 5.4 |
| De-silicated 30% | 40.4 | 63.4 | 25.6 | 5.4 | 6.3 | 3.1 |
| Natural Erionite | | | | | | |
| As is | 8.8 | | | | | |
| De-aluminized 38% | 40.1 | 27.0 | 10.8 | 15.6 | 3.7 | 9.9 |
| Then de-silicated 16% | 38.6 | 38.7 | 14.9 | 10.7 | 6.4 | 6.5 |
| Then $NH_4Cl$ Exchanged | 46.4 | 24.3 | 11.3 | 18.0 | 3.6 | 13.5 |
| Silica Alumina (7.6% $Al_2O_3$) | | | | | | |
| As is (S.A. 477 m²/g) | 61.6 | 56.4 | 34.7 | 8.9 | 13.5 | 4.4 |
| Steamed 6 hrs., 1300°F. | 33.6 | 64.3 | 21.6 | 4.4 | 7.0 | 0.6 |

*E. Texas light gas oil, 900°F., 2 cat/oil, 10 min.

EXAMPLE 16

In Table 21 there is set forth a comparison of alumina

TABLE 19

MID-CONTINENT WIDE-CUT GAS OIL CRACKING

| | Cat/Oil Ratio | WHSV | Conversion Wt. % | Selectivity, $C_5$ + Gaso. | Product Distribution, Wt.% $C_1$–$C_3$ | $C_4$ | Coke | $C_5+$ Gaso. |
|---|---|---|---|---|---|---|---|---|
| 42% Dealuminized REY | | | | | | | | |
| Fresh | 1 | 6 | 72.6 | 58.4 | 9.4 | 20.4 | 0.4 | 42.4 |
| Regenerated once | 1 | 6 | 61.5 | 59.3 | 7.4 | 14.6 | 3.0 | 36.5 |
| Regenerated twice | 1 | 6 | 71.9 | 58.6 | 8.6 | 18.5 | 2.7 | 42.1 |
| Fresh | 1 | 6 | 69.1 | 56.9 | 8.7 | 17.8 | 3.3 | 39.3 |
| Regenerated once | 1 | 6 | 66.0 | 56.5 | 8.5 | 16.9 | 3.3 | 37.3 |
| REY | | | | | | | | |
| Fresh | 1 | 6 | 82.8 | 48.8 | 11.7 | 24.0 | 6.7 | 40.4 |
| Regenerated once | 1 | 6 | 81.3 | 46.9 | 12.3 | 25.1 | 5.8 | 38.1 |
| Fresh | 0.5 | 12 | 73.9 | 55.8 | 9.5 | 20.0 | 3.2 | 41.2 |
| Regenerated once | 0.5 | 12 | 71.0 | 56.1 | 9.4 | 18.9 | 3.0 | 39.8 | removal from erionite with $CrCl_3$ and alumina removal with EDTA.

TABLE 21

| | | | Via 1.0 N $CrCl_3$ | Via EDTA |
|---|---|---|---|---|
| Step 1 | Aluminum Removal From Erionite % | | 38 | 44 |
| | n-Hexane Adsorption, Wt. % | | 9.4 | 6.7 |
| | Cyclohexane Adsorption, Wt. % | | 3.7 | 3.6 |
| Step 2 | Silica Removal, Wt. %* | | 16 | 22 |
| | Analyses, Wt. % | | | |
| | K | 3.7 | 1.7 | 2.1 |
| | Na | 3.3 | 3.8 | 4.4 |
| | Ca | 3.0 | 0.15 | 0.08 |
| | Mg | 0.57 | 2.12 | 0.09 |
| | $SiO_2$ | 66.8 | 78.0 | 79.8 |

TABLE 21-continued

|  | Via 1.0 N CrCl$_3$ |  | Via EDTA |
|---|---|---|---|
| Al$_2$O$_3$ | 15.4 | 13.4 | 13.3 |
| Fe | 1.95 | 2.12 | 0.09 |
| Cr | — | 0.18 | — |
| Ash | 81.1 | 91.4 | 85.0 |
| SiO$_2$/Al$_2$O$_3$ Ratio | 7.3 | 9.9 | 9.8 |
| Eq. K/Al | 0.31 | 0.17 | 0.20 |
| Eq. Na/Al | 0.48 | 0.63 | 0.73 |
| Eq. Ca/Al | 0.50 | 0.03 | 0.02 |
| Eq. Mg/Al | 0.16 | 0.07 | 0.03 |
| n-Hexane Adsorption, Wt. %** | 5.2 | 10.7 | 5.8 |
| Cyclohexane Adsorption, Wt. %** | 1.7 | 6.8 | 1.2 |

*4 g. of zeolite from Step 1 contacted with 600 cc. refluxing 1.0 N NaCl for one hour, filtered, repeated two more times.
**determined at 20 mm Hg and 25°C.

It will be noted that while EDTA is equally effective for alumina removal and provides substantially the same dealuminized zeolite Y samples in the as is and sodium back exchanged forms.

TABLE 22

PROPANE DEHYDROGENATION
Atmospheric Pressure, 1 cc. Cat., 10 cc. Propane/Min.

| Catalyst | Commercial Catalyst | | 32% Dealuminized Zeolite Y | | | | 62% Dealuminized Zeolite Y NaCl Exch. | | Cr[−96% Al]Y NaCl Exch. | |
|---|---|---|---|---|---|---|---|---|---|---|
| | | | As Is | | NaCl Exch. | | | | | |
| Wt. % Cr. | | 8.58 | | 7.1 | | 5.7 | | 5.33 | | 1.40 |
| g Cr in 1 cc. Cat. | | 0.071 | | 0.043 | | 0.031 | | 0.021 | | 0.004 |
| Propane Conversion | C$_3$= | C$_1$+C$_2$ | C$_3$= | C$_1$+C$_2$ | C$_3$= | C$_1$+C$_2$ | C$_3$= | C$_1$+C$_2$ | C$_3$= | C$_1$+C$_2$ |
| 850°F | 1.5 | 0.1 | 2.0 | Nil | 3.3 | <0.1 | 3.9 | 0.1 | 0.7 | 0.1 |
| 900°F. | 2.2 | 1.0 | 2.1 | <0.1 | 4.2 | 0.1 | 5.5 | 0.2 | 2.0 | 0.1 |
| 950°F. | 4.3 | 0.2 | 4.1 | 0.3 | 6.0 | 0.2 | 9.5 | 0.6 | 2.0 | 0.1 |
| 1000°F. | 9.8 | 0.6 | 6.1 | 1.2 | 8.3 | 0.3 | 12.3 | 1.2 | 6.0 | 0.5 |
| 1050°F. | 17.6 | 2.0 | 8.4 | 3.9 | 11.7 | 0.7 | 17.1 | 3.2 | 7.8 | 1.0 | silica/alumina ratio of the erionite treated sample that for some unexplainable reason the sorption properties of the product provided by EDTA treatment are substantially inferior to those provided by treatment with CrCl$_3$. Thus, the normal hexane sorption for the EDTA treated sample is little more than ½ the value obtained for the CrCl$_3$ sample. The cyclohexane sorption value after subsequent silica removal is about 1/5 the value obtained for the CrCl$_3$ treated sample after silica removal.

Dealuminized aluminosilicate compositions containing chromium prepared by the present method are useful in both hydrogenation and dehydrogenation of organic compounds especially paraffins. At temperatures between 200° and 800°F. and between pressures of 0 and 3000 psig., a dealuminized zeolite, e.g., dealuminized zeolite Y can be employed to catalyze the hydrogenation of propylene. Similarly, by employing higher temperatures generally between the temperatures of 800° and 1300°F. and pressures between 0 and 700 psig., hydrocarbons, e.g., paraffins, can be dehydrogenated. In Table 22 below, there is set forth a comparison of propane dehydrogenation over various The propane dehydrogenation is compared with a commercial catalytic substance comprising two volumes of silica gel powder mixed with 1 volume of a substance comprising a Cr$_2$O$_3$ activated alumina supported catalyst containing 19 percent by weight Cr$_2$O$_3$. The zeolite samples were back exchanged with sodium to decrease the cracking activity of the zeolite. It will be noted that at lower temperatures in particular the dealuminized silica/alumina composition provides a desirable amount of propylene with good selectivity.

EXAMPLE 17

In order to more specifically establish the criticality of the required limitations of the present invention, that is to remove alumina from a crystalline aluminosilicate without substantially destroying crystallinity, the following tests were conducted on Linde 13X (to establish criticality of silica/alumina mole ratio); erionite (to establish criticality of the chromium compound employed); Linde 5A (to establish criticality of the chromium compound and silica/alumina ratio); and zeolite NaY (to establish criticality of temperature, chromium to aluminum atomic ratio, pH and dilution). The results appear in Table 23.

TABLE 23

| Critical Variable Starting Zeolite | SiO$_2$/Al$_2$O$_3$ Ratio Linde 13X | | Cr Compound Erionite | | Cr Compound & SiO$_2$/Al$_2$O$_3$ Ratio Linde 5A | | | Temp. Cr/Al pH NaY | | | Dilution & Cr/Al |
|---|---|---|---|---|---|---|---|---|---|---|---|
| g | Base | 50 | 50 | Base | 20 | Base | 17.8 | 17.8 | Base | 20 | 20 | 20 | 4 |
| Chromium Compound | CrCl$_3$ | CrCl$_3$ | | (NH$_4$)$_2$CrO$_4$ | | (NH$_4$)$_2$CrO$_4$ | Cr(OAC)$_3$ | | | | CrCl$_3$ | |
| Solution Normality | 1.0 | 0.5 | | 0.7 | | 2.9 | 1.0$^{(1)}$ | | 1.0 | 1.0 | 1.0 | 0.1 |
| pH | 2.1 | 2.5 | | 7.6 | | 7.2 | 4.5 | | 2.1 | 2.1 | 4.0$^{(2)}$ | 2.4 |

TABLE 23-continued

| Critical Variable Starting Zeolite | SiO$_2$/Al$_2$O$_3$ Ratio Linde 13X | | Cr Compound Erionite | | Cr Compound & SiO$_2$/Al$_2$O$_3$ Ratio Linde 5A | | | Temp. Cr/Al pH NaY | | | | Dilution & Cr/Al |
|---|---|---|---|---|---|---|---|---|---|---|---|---|
| g | Base | 50 | 50 | Base | 20 | Base | 17.8 | 17.8 | Base | 20 | 20 | 20 | 4 |
| ml. | | 750 | 750 | | 600 | | 240 | 240 | | 200 | 120 | 120 | 400 |
| Temp. (approx.)°C. | | 100 | 100 | | 100 | | 100 | 100 | | 70 | 100 | 100 | 100 |
| Contact Time, Hours | | 2 | 2 | | 2 | | 2 | 2 | | 2 | 2 | 2 | 2 |
| Number of Contacts | | 1 | 1 | | 2 | | 1 | 1 | | 1 | 1 | 1 | 1 |
| Ratio, Cr in Solution/Al In Zeolite | | 0.8 | 0.4 | | 7.1 | | 0.6 | 0.6 | | 1.0 | 0.6 | 0.6 | 6.0 |
| Washed, Dried Zeolite Code | A | B | C | D | E | F | G | H | I | J | K | L | M |
| Analysis, Wt.% | | | | | | | | | | | | | |
| SiO$_2$ | 48.7 | 60.7 | 48.4 | 66.8 | 75.3 | 44.2 | 47.5 | 28.4 | 63.8 | 66.0 | 65.9 | 61.4 | 77.1 |
| Al$_2$O$_3$ | 52.8 | 22.0 | 31.8 | 15.4 | 17.3 | 38.2 | 40.8 | 23.8 | 21.0 | 18.5 | 17.4 | 19.1 | 9.9 |
| Na | 14.9 | 0.06 | 0.1 | 3.3 | 0.7 | 4.7 | 1.4 | 3.0 | 10.2 | 2.2 | 2.4 | 3.2 | 0.8 |
| Ca | — | — | — | 3.0 | — | 8.8 | 7.6 | 5.8 | — | — | — | — | — |
| Cr | — | 13.2 | 12.7 | — | 0.03 | — | 0.04 | 18.8 | — | 6.9 | 7.6 | 8.9 | 6.9 |
| Ash | 81.7 | — | 79.6 | 81.1 | 87.5 | >95 | 67.5 | 67.5 | 80 | 81.6 | 82.4 | 76.9 | 78.2 |
| Alumina Removal, Wt. % | — | 46 | 2 | — | NIL | — | NIL | NIL | — | 15 | 20 | 5 | 61 |
| SiO$_2$/Al$_2$O$_3$ Ratio | 2.5 | 4.7 | 2.6 | 7.3 | 7.4 | 2.0 | 2.0 | 2.0 | 5.2 | 6.1 | 6.4 | 5.5 | 13.2 |
| n-Hexane Adsorption, Wt.% | 15.8 | 5.9 | — | 5.2 | 6.8 | 12.6 | 7.6 | 5.6 | 17.5 | 11.8 | 15.5 | 14.1 | 8.3 |
| Cyclohexane Adsorption Wt.% | 18.2 | — | 8.6 | 1.7 | — | 0.4 | — | — | 18.3 | 12.8 | 13.5 | 14.4 | 11.3 |
| Crystallinity, X-ray | 100 | Amorphous | — | — | 100 | 55 | 15 | 100 | 45 | 60 | 70 | 30 | |

EXAMPLE 18

To establish the absolute minimum dilution for the chromium salt solution as being greater than 0.01 Normal, the procedure for Example 17 was repeated for zeolite Y, code M (Table 23), wherein the solution of CrCl$_3$ used had a normality of 0.01. It is observed from the data thus generated (Table 23A) that, although chromium is exchanged into the zeolite structure at the expense of sodium as one would expect from the prior art, there is absolutely no alumina removal.

TABLE 23A

| Critical Variable | Dilution |
|---|---|
| Starting Zeolite | NaY |
| g. | 4 |
| Chromium Compound | CrCl$_3$ |
| Solution Normality | 0.01 |
| pH | 3.2 |
| ml. | 2400 |
| Temperature (approx.) °C. | 100 |
| Contact Time, Hours | 2 |
| Number of Contacts | 1 |
| Ratio, Cr in solution/Al in Zeolite | 0.6 |
| Analysis, Wt.% | |
| SiO$_2$ | 62.6 |
| Al$_2$O$_3$ | 21.4 |
| Na | 1.8 |
| Cr | 7.9 |
| Ash | 83.3 |
| Alumina Removal, Wt.% | NIL |
| SiO$_2$/Al$_2$O$_3$ Ratio | 5.0 |
| n-Hexane Adsorption, Wt.% | 10.5 |
| Crystallinity, X-Ray | 90 |

Generally speaking, the compositions prepared by the treatment pursuant to the present invention can, if desired, be ion exchanged into a metal form, a hydrogen form or a hydrogen precursor form, in accordance with known techniques as described, for instance, in U.S. Pat. No. 3,140,253. Dealuminized compositions can be used for a wide variety of hydrocarbon conversion processes including isomerization, disproportionation, hydration of olefins, amination of olefins, oxidation, dehydrogenation, dehydration of alcohols, desulfurization, hydrofinishing, hydrogenation, reforming, hydrocracking, polymerization and the like. The temperatures, pressures, space velocities and other reaction conditions for these processes are those generally known in the art and described in numerous patents and publications. The reactants also are those described in the art. For reactions involving a hydrogenation or dehydrogenation function, it is desirable that the catalytic substance include a hydrogenation/dehydrogenation component suitably a Group VIII metal, especially a metal of the platinum series.

In the above specification, reference is made to a zeolite identified as ZSM-4. ZSM-4 is a relatively new zeolite which, in its as synthesized aluminosilicate form, has the following composition, expressed in terms of mole ratios of oxides:

$$0.9 \pm 0.2 \, M_{2/n}O : Al_2O_3 : 3\text{-}20 \, SiO_2$$

where M is a mixture of tetramethylammonium cations and alkali metal cations, especially sodium. Generally, the tetramethylammonium cations comprise between 1 and 50 percent of the cations in the as synthesized form. The particular ZSM-4 zeolite for use in the dealuminization process of this invention has a silica/alumina mole ratio of above 3 to about 12. ZSM-4 has a distinctive X-ray diffraction pattern which further identified it from other known zeolites. The original alkali metal cations of ZSM-4 can be exchanged by ion exchange with other ions to form species of the zeolite which have exceptional catalytic properties.

ZSM-4 is generally prepared by forming a mixture of alumina, silica, sodium oxide, water and tetramethylammonium compounds such that the mixture has a composition, in terms of mole ratios of oxides, falling within the following range:

$$\frac{\text{Alkali Metal Oxide}}{\text{Alkali Metal Oxide} + R_2O} \quad 0.31 \text{ to} < 1$$

$$\frac{R_2O + \text{Alkali Metal Oxide}}{SiO_2} \quad .05 \text{ to } .90$$

$$\frac{SiO_2}{Al_2O_3} \quad 3 \text{ to } 60$$

$$\frac{H_2O}{R_2O + \text{Alkali Metal Oxide}} \quad 15 \text{ to } 600$$

wherein R is a tetramethylammonium cation. The mixture is maintained under conditions of temperature and pressure until crystals are formed which crystals are separated and recovered.

Members of the family of ZSM-4 zeolites possess a definite distinguishing crystalline structure whose X-ray diffraction pattern has the following values:

TABLE 24

| Interplanar Spacing d(A) | Relative Intensity |
|---|---|
| 9.1 ± .2 | vs |
| 7.94 ± .1 | mw |
| 6.90 ± .1 | m |
| 5.97 ± .07 | s |
| 5.50 ± .05 | mw |
| 5.27 ± .05 | mw |
| 4.71 ± .05 | mw |
| 4.39 ± .05 | w |
| 3.96 ± .05 | w |
| 3.80 ± .05 | s |
| 3.71 ± .05 | m |
| 3.63 ± .05 | m |
| 3.52 ± .05 | s |
| 3.44 ± .05 | m |
| 3.16 ± .05 | s |
| 3.09 ± .05 | m |
| 3.04 ± .05 | m |
| 2.98 ± .05 | m |
| 2.92 ± .05 | s |

These values were determined by standard techniques. The radiation was the K-alpha doublet of copper, and a Geiger counter spectrometer with a strip chart pen recorder was used. The peak heights, I, and the positions as a function of 2 times theta, where theta is the Bragg angle, were read from the spectrometer chart. From these, the relative intensities, $100 I/I_o$, where $I_o$ is the intensity of the strongest line or peak, and $d$(obs.), the interplanar spacing in A, corresponding to the recorded lines, were calculated. In Table 24, the relative intensities are given in terms of the symbols vs = very strong, $s$ = strong, m = medium, and mw = medium weak. It should be understood that this X-ray diffraction pattern is characteristic of all the species of ZSM-4 compositions. Ion exchange of the sodium ion with another cation reveals substantially the same pattern with some minor shifts in interplanar spacing and variation in relative intensity.

ZSM-5 compositions can be identified, in terms of mole ratios of oxides, as follows:
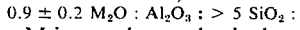
where M is a cation and $n$ is the valence of said cation. In a preferred synthesized form the zeolite has a formula, in terms of mole ratios of oxides, as follows:
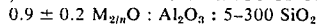
wherein M is selected from the group consisting of a mixture of alkali metal cations, especially sodium, and tetraalkylammonium cations, the alkyl groups of which preferably contain 2–5 carbon atoms. Of course, the ZSM-5 zeolite for use in the present dealuminization process has a silica/alumina mole ratio of greater than 5 to about 12.

The original cations can be replaced in accordance with techniques well-known in the art, at least in part, by ion exchange with other cations. Preferred replacing cations include tetraalkylammonium cations, metal ions, ammonium ions, hydrogen ions and mixtures of the same. Particularly preferred cations are those which render the zeolite catalytically active, especially for hydrocarbon conversion. These include hydrogen, rare earth metals, aluminum, metals of Group II and VIII of the Periodic Table and manganese.

Members of the family of zeolites designated herein as ZSM-5 have an exceptionally high degree of thermal stability thereby rendering them particularly effective for use in processes involving elevated temperatures. In this connection, ZSM-5 zeolites appear to be one of the most stable families of zeolites known to date.

Members of the family of ZSM-5 zeolites possess a definite distinguishing crystalline structure whose X-ray diffraction pattern shows the following significant lines:

TABLE 25

| Interplanar Spacing d(A) | Relative Intensity |
|---|---|
| 11.1 ± 0.3 | s |
| 10.0 ± 0.3 | s |
| 7.4 ± 0.2 | w |
| 7.1 ± 0.2 | w |
| 6.3 ± 0.2 | w |
| 6.04 ± 0.2 | w |
| 5.97 ± 0.2 | w |
| 5.69 ± 0.1 | w |
| 5.56 ± 0.1 | w |
| 5.01 ± 0.1 | w |
| 4.60 ± 0.1 | w |
| 4.35 ± 0.1 | w |
| 4.25 ± 0.1 | w |
| 3.85 ± 0.1 | vs |
| 3.75 ± 0.05 | s |
| 3.71 ± 0.05 | s |
| 3.64 ± 0.05 | m |
| 3.04 ± 0.05 | w |
| 2.99 ± 0.05 | w |
| 2.94 ± 0.05 | w |

These values were determined by the same technique used to determine the X-ray values of Table 24, with the relative intensities given in terms of the symbols s= strong m = medium, w = weak, and vs = very strong.

What is claimed is:

1. A method of removing alumina from a crystalline aluminosilicate having a silica/alumina mole ratio of from above 3 to about 12 which comprises heating said aluminosilicate to a temperature of greater than 50°C to about 100°C in the presence of positive trivalent chromium ions in aqueous solution of above 0.01 Normal of a chromium salt of a mineral acid whereby the pH is less than 3.5 such that the atomic ratio of chromium in the solution to aluminum in the aluminosilicate is greater than 0.5 for a time sufficient to remove alumina.

2. The method of claim 1 wherein said crystalline aluminosilicate is a zeolite.

3. The method of claim 2 wherein said zeolite is one selected from the group consisting of erionite, phillipsite, clinoptilolite, zeolites T, Y, ZSM-4, ZSM-5 and mordenite.

4. The method of claim 1 wherein said aluminosilicate is refluxed with said positive trivalent form of chromium until at least 10 percent of the alumina is removed.

5. The method of claim 1 wherein the crystalline aluminosilicate contains alkali metal cations.

6. The method of claim 5 wherein the crystalline aluminosilicate is also contacted with a salt of a cation which is desired to be exchanged for the alkali metal cations in the crystalline aluminosilicate, said cation to be exchanged for the alkali metal cations being selected from the group consisting of hydrogen, ammonium, alkylammonium, rare earth metal, aluminum, manganese, metals of Groups II and VIII of the Periodic Table of Elements and mixtures thereof.

7. The method of claim 1 wherein after the crystalline aluminosilicate has been dealuminized, it is treated with a solution of an alkali metal salt or ammonium salt to remove silica therefrom.

8. The method of claim 5 wherein said crystalline aluminosilicate is a form of zeolite Y.

9. The method of claim 6 wherein said zeolite is a form of zeolite Y.

10. The method of claim 7 wherein the crystalline aluminosilicate is treated with an aqueous solution of a sodium salt.

11. The method of claim 10 wherein said sodium salt is NaCl.

12. The method of claim 1 wherein said chromium salt is $CrCl_3$.

13. The method of claim 1 wherein said chromium salt is $Cr(NO_3)_3$.

14. The method of claim 1 wherein said chromium salt is $CrK(SO_4)_2$.

* * * * *

UNITED STATES PATENT AND TRADEMARK OFFICE
CERTIFICATE OF CORRECTION

PATENT NO. : 3,937,791

DATED : February 10, 1976

INVENTOR(S) : WILLIAM E. GARWOOD, NAI YUEN CHEN and STANLEY J. LUCKI

It is certified that error appears in the above-identified patent and that said Letters Patent are hereby corrected as shown below:

Column 25, line 50      "$0.9 \pm 0.2\ M_2O : Al_2O_3 : >5\ SiO_2$"

should read

--$0.9 \pm 0.2\ M_{\frac{2}{n}}O : Al_2O_3 : >5\ SiO_2$--

Signed and Sealed this

Tenth Day of August 1976

[SEAL]

Attest:

RUTH C. MASON
*Attesting Officer*

C. MARSHALL DANN
*Commissioner of Patents and Trademarks*